US012778700B2

(12) United States Patent
Hladio et al.

(10) Patent No.: US 12,778,700 B2
(45) Date of Patent: Nov. 3, 2026

(54) SYSTEMS AND METHODS TO PERFORM ROBOTIC RETRACTION AND ROBOTIC DISTRACTION

(71) Applicant: INTELLIJOINT SURGICAL INC., Kitchener (CA)

(72) Inventors: Andre Novomir Hladio, Waterloo (CA); Samantha Mccabe, Kitchener (CA); Joseph Arthur Schipper, Kitchener (CA); Mark Pringle-Rigby, Waterloo (CA)

(73) Assignee: INTELLIJOINT SURGICAL INC., Kitchener (CA)

( * ) Notice: Subject to any disclaimer, the term of this patent is extended or adjusted under 35 U.S.C. 154(b) by 972 days.

(21) Appl. No.: 17/591,073

(22) Filed: Feb. 2, 2022

(65) Prior Publication Data

US 2022/0241040 A1 Aug. 4, 2022

Related U.S. Application Data

(60) Provisional application No. 63/144,635, filed on Feb. 2, 2021.

(51) Int. Cl.

| | |
|---|---|
| ***A61B 17/02*** | (2006.01) |
| ***A61B 17/30*** | (2006.01) |
| ***A61B 17/32*** | (2006.01) |
| ***A61B 34/00*** | (2016.01) |
| ***A61B 34/10*** | (2016.01) |
| ***A61B 34/20*** | (2016.01) |
| ***A61B 34/30*** | (2016.01) |

(52) U.S. Cl.

CPC .......... *A61B 34/70* (2016.02); *A61B 17/0206* (2013.01); *A61B 17/025* (2013.01); *A61B 34/10* (2016.02); *A61B 34/20* (2016.02); *A61B 34/30* (2016.02); *A61B 2034/104* (2016.02); *A61B 2034/105* (2016.02); *A61B 2034/107* (2016.02); *A61B 2034/2055* (2016.02)

(58) Field of Classification Search

CPC ........ A61B 17/02; A61B 17/025; A61B 34/32

See application file for complete search history.

(56) References Cited

U.S. PATENT DOCUMENTS

| | | | | |
|---|---|---|---|---|
| 10,166,019 | B2 * | 1/2019 | Nawana | A61B 34/25 |
| 2016/0030063 | A1 * | 2/2016 | Pack | A61B 17/1714 606/96 |
| 2022/0151714 | A1 * | 5/2022 | Zehavi | A61B 17/0206 |
| 2022/0163409 | A1 * | 5/2022 | Dumpe | A61B 17/8866 |
| 2024/0065783 | A1 * | 2/2024 | Kang | A61B 34/74 |
| 2024/0081934 | A1 * | 3/2024 | Khurana | A61B 34/32 |

* cited by examiner

*Primary Examiner* — Nicholas W Woodall

(57) ABSTRACT

Systems and methods for robotic retraction or robotic distraction are disclosed such as for a surgical procedure. An example system is a localization system to automatically position a trackable surgical retractor or distraction with respect to a patient comprising a patient tracking element adapted to be coupled to a patient; a processing unit configured to: track the poses of the patient via the patient tracking element, and the trackable surgical retractor or distractor; and command a robotic manipulator to move a tip of the trackable surgical retractor or distractor coupled to the manipulator from a first position, in engagement with the patient, to a second position while remaining in engagement with the patient.

23 Claims, 7 Drawing Sheets

SYSTEMS AND METHODS TO PERFORM ROBOTIC RETRACTION AND ROBOTIC DISTRACTION

CROSS-REFERENCE

This application claims the benefit of U.S. Provisional Application No. 63/144,635, filed Feb. 2, 2021, the entire contents of which are incorporated herein by reference.

FIELD

This disclosure relates to localization and robotic procedures in a surgical application and more particularly to systems and methods to perform robotic retraction and robotic distraction.

BACKGROUND

Localization systems track objects in a three dimensional space. In a surgical procedure context such as an operating room, objects may include surgical tools, and parts of patient anatomy (e.g. bones, etc.) During some surgical procedures, retraction is used to move a portion of patient anatomy. Retraction is typically maintained for a period of time as well. Distraction is a related activity to move a portion of patient anatomy, for example a bone.

Robot manipulators are used in surgery to perform all or portions of a procedure. Robot manipulators are operable to move tools, for example, via a trajectory or path, and to engage with patient anatomy when performing a portion of a procedure.

It is desirable to provide a system and method for robotic retraction and robotic distraction.

SUMMARY

There are provided systems and methods to perform robotic retraction and robotic distraction. An example system is a localization system to automatically position a trackable surgical tool (e.g. a retractor or distractor) with respect to a patient comprising a patient tracking element adapted to be associated with a patient to provide patient pose data; and a processing unit configured to: track the poses of the patient via the patient tracking element, and the trackable surgical tool; and command a robotic manipulator to move a tip of the trackable surgical tool coupled to the manipulator from a first position, in engagement with the patient, to a second position while remaining in engagement with the patient.

In an embodiment, there is provided a method to automatically perform robotic retraction or distraction with respect to a patient. In the embodiment, the method comprises, by a processing unit: a) tracking the poses of: i) a patient via a patient tracking element adapted to be associated with a patient to provide patient pose data; and ii) a trackable tool for surgical retraction or distraction; and b) commanding a robotic manipulator to move a tip of the trackable tool coupled to the manipulator from a first position, in engagement with the patient, to a second position while remaining in engagement with the patient.

In an embodiment, there is provided a system to automatically perform robotic retraction or distraction with respect to a patient. In the embodiment, the system comprises: a) a patient tracking element adapted to be associated with a patient to provide patient pose data; and b) a processing unit configured to: (a) track the poses of: i) the patient via the patient tracking element; and ii) a trackable tool for surgical retraction or distraction; and (b) command a robotic manipulator to move a tip of the trackable tool coupled to the manipulator from a first position, in engagement with the patient, to a second position while remaining in engagement with the patient.

DETAILED DESCRIPTION

Retraction typically denotes an act of drawing back or pulling. Herein retraction includes other acts to move a portion of anatomy, for example, a pushing act. Also described herein are embodiments related to distraction. Distraction may reference a force applied to separate bony fragments or joint surfaces. The separation may be without rupture of binding ligaments and without displacement. Aspects and/or features described in relation to retraction apply to distraction and vice versa unless the context requires otherwise.

Figure 1:
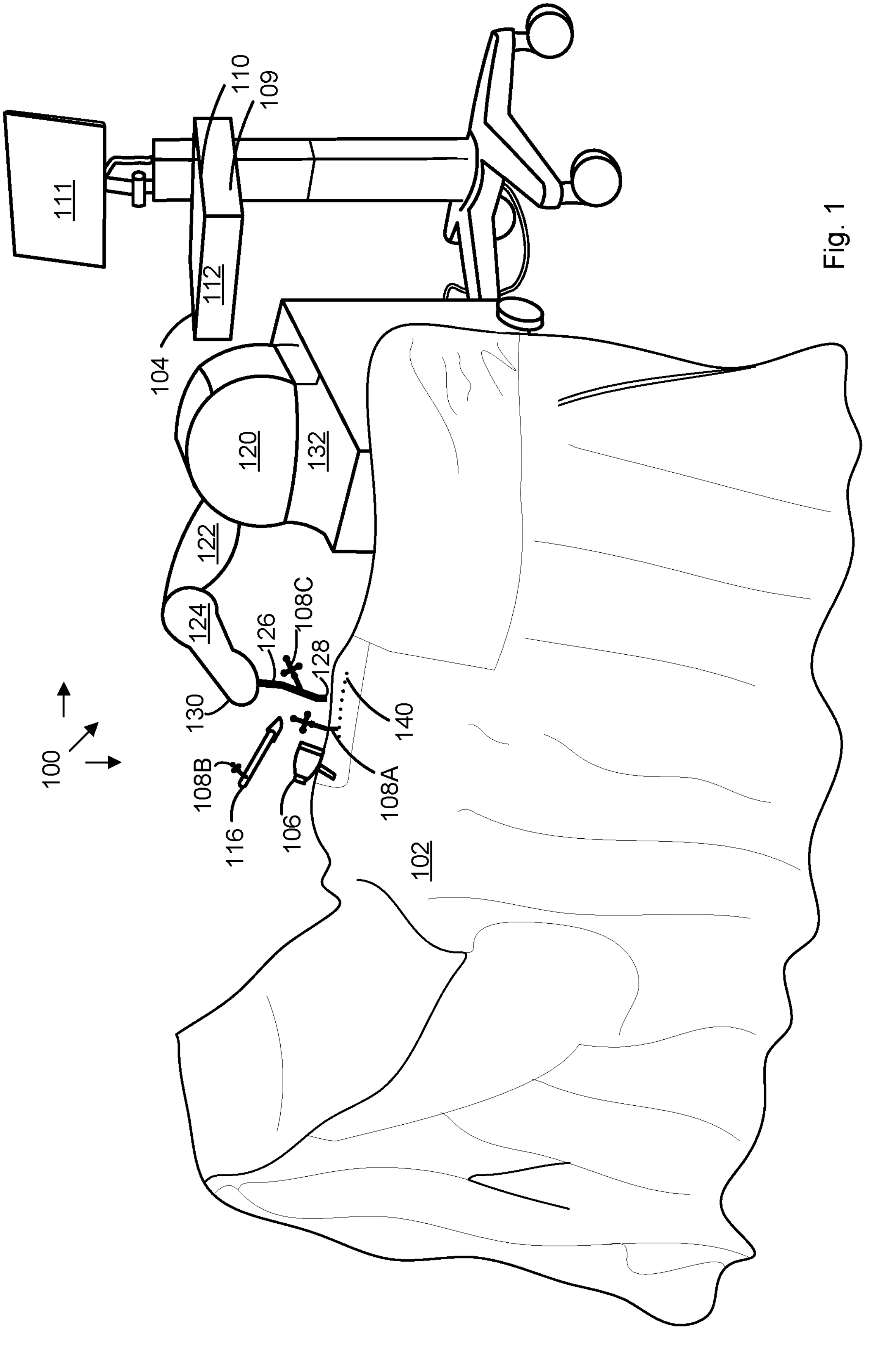
FIG. 1 is an illustration of an operating room including a system to perform a robotic retraction in accordance with an embodiment.

FIG. 1 is an illustration of a system 100 to perform a robotic retraction on a patient 102 in accordance with an embodiment. System 100 comprises a processing unit 104, an optical sensor 106 and a plurality of tracking elements 108A, 108B and 108C. Tracking elements provide respective signals to optical sensor 106 (when in its field of view), which in turn communicates optical tracking data to processing unit 104 via wired or wireless means. The respective tracking elements provide pose data for determining respective poses of objects associated with the respective tracking elements.

Optical sensor 106, in the present embodiment, is configured to couple with the patient 102 such as to a bone. In the present embodiment it is configured to couple to a pelvis (not shown) for performing a total hip arthroplasty (THA) procedure. Tracking element 108A is configured to be coupled to patient 102, for example, to attach to a bone namely a femur (not shown) for performing a total hip arthroplasty (THA) procedure. Tracking elements 108B and 108C are configured to be coupled to a respective tool as described further.

A patient tracking element may be fixed to a patient bone using bone screws or other bone engaging fasteners. A patient tracking element may be associated with a patient in other ways. For example, fiducials may be applied to skin such as using an adhesive or a cuff or sleeve; or a table or other fixed mounted tracker may be used in association with the patient, preferably where the patient (or a material portion thereof to be tracked) is maintained through the procedure to avoid repeated registration.

As is known, the pose of a tracking element is useful to determine a pose of an object to which the tracking element is coupled. A tracking element may be integrally formed with or attached to an object in a position that is known to processing unit 104. A tracking element may be attached in an unknown position that is then taught to processing unit 104.

As is known, a registration step may be performed using known methods to register a patient in 3D space to the processing unit. Registration permits system 100 to determine relative positions of objects with one another such as tools to the patient.

Processing unit 104 may be configured to receive 3D data 109 (e.g. image data, for example a segmented computerized tomography (CT) scan) representing a portion of the patient for storing to storage device 110 and for display on display device 111. Such 3D data 109 may be generated using various imaging modalities and be defined using applicable standards and/or techniques. The 3D data 109 may be registered to processing unit 104 such as using known methods to relate the 3D data 109 to the patient in 3D space and/or to the tools in 3D space. As is known, as an object is tracked, its location relative to the 3D data may be displayed (e.g via an overlay or other manner).

Processing unit 104 can be coupled to a keyboard 112 to receive user input. The keyboard and other input devices may be coupled via wired or wireless means. Input devices may include buttons, foot pedal(s), microphone, etc.

Processing unit 104 is configured to track tools for the THA procedure using tracking elements 108B and 108C. Tracking element 108B is configured to couple with a scalpel 116 and tracking element 108C is configured to couple to a surgical tool operated by a robot manipulator 120. Scalpel 116 is an example of a soft tissue cutting tool.

Robot manipulator 120 comprises articulating arms 122, 124, which are configured to move one or more tools at the distal end thereof, such as a trackable surgical retractor 126 having a retractor tip 128. Tracking element 108C is configured to couple to trackable surgical retractor 126. It will be understood that the couplings for the tracking elements may enable removing of the tracking elements and replacement at a same location. Couplings may be kinematic couples that enforce a particular coupling location or position.

In accordance with the embodiment, robot manipulator 120 comprises a tool sensor 130 (or retractor sensor) to provide tool sensor data (e.g. retractor sensor data) to processing unit 104.

In an embodiment, robot manipulator 120 comprises a processing unit 132 for operating the articulating arms 122, 124 and one or more tools at the distal end thereof such as retractor 126. Retractor sensor data may be communicated via processing unit 132 to processing unit 104 or may be communicated directly (e.g. not via processing unit 132).

In accordance with the embodiment, processing unit 104 is configured to (e.g. via software) track the poses of: the patient via the patient tracking element, and the trackable surgical retractor; and command a robotic manipulator to move a retractor tip of the trackable surgical retractor coupled to the manipulator from a first position, in engagement with the patient, to a second position while remaining in engagement with the patient. As described further, in accordance with an embodiment, the first position may be determined relative to an incision location.

In accordance with the embodiment, scalpel 106 is an incision indicating tool, when tracked during cutting or at another time (e.g. before or after cutting), the location of an incision 140 is indicated to processing unit 104. In an embodiment, processing unit 104 is configured to provide workflow to guide a surgical procedure. A portion of such workflow may relate to registration steps, retractions steps, tracking element coupling steps, etc. In an example, workflow is provided to instruct a user to operate the system 100 to capture the location of the incision (e.g. which location may be related to the patient and/or patient 3D data). A button or key, etc. may be invoked to signal the processing unit to track the incision indicating tool (e.g. its tip) as it makes the incision or traces its location.

In an example, a probe tip of a trackable probe tool (not shown) rather than a scalpel or cutting tool, is tracked and indicates the incision location 140. The trackable probe tool may trace along the incision location or indicate two or more points there along to processing unit 104 for processing to define the incision location. The trackable probe tool can indicate the incision location 140 after the incision is made, or can indicate the intended location of incision 140 before the incision is made.

In an example, the incision indicating tool may indicate a location that is less than the whole length of the actual (or proposed) incision and only indicate a portion where it is desired to have the retractor tip engage with the patient.

Accordingly, the incision indicating tool can be one of: i) a soft tissue cutting tool and the incision location is determined in response to the soft tissue cutting tool making an incision or tracing an incision; and ii) a probe and the incision location is determined in response to the probe indicating the incision location.

Retraction (and distraction) relate to moving a portion of the patient's anatomy. In the present embodiment of FIG. 1, retraction is desired to open a surgical site following an incision. In the example, a retractor is positioned such that the tip thereof is at a first position in engagement with the patient and is moved to a second position while remaining in engagement with the patient. In an example the first position may be a portion along the incision. Thus, processing unit 104 can be configured to determine the first position relative to the incision location as described further.

Figure 2:
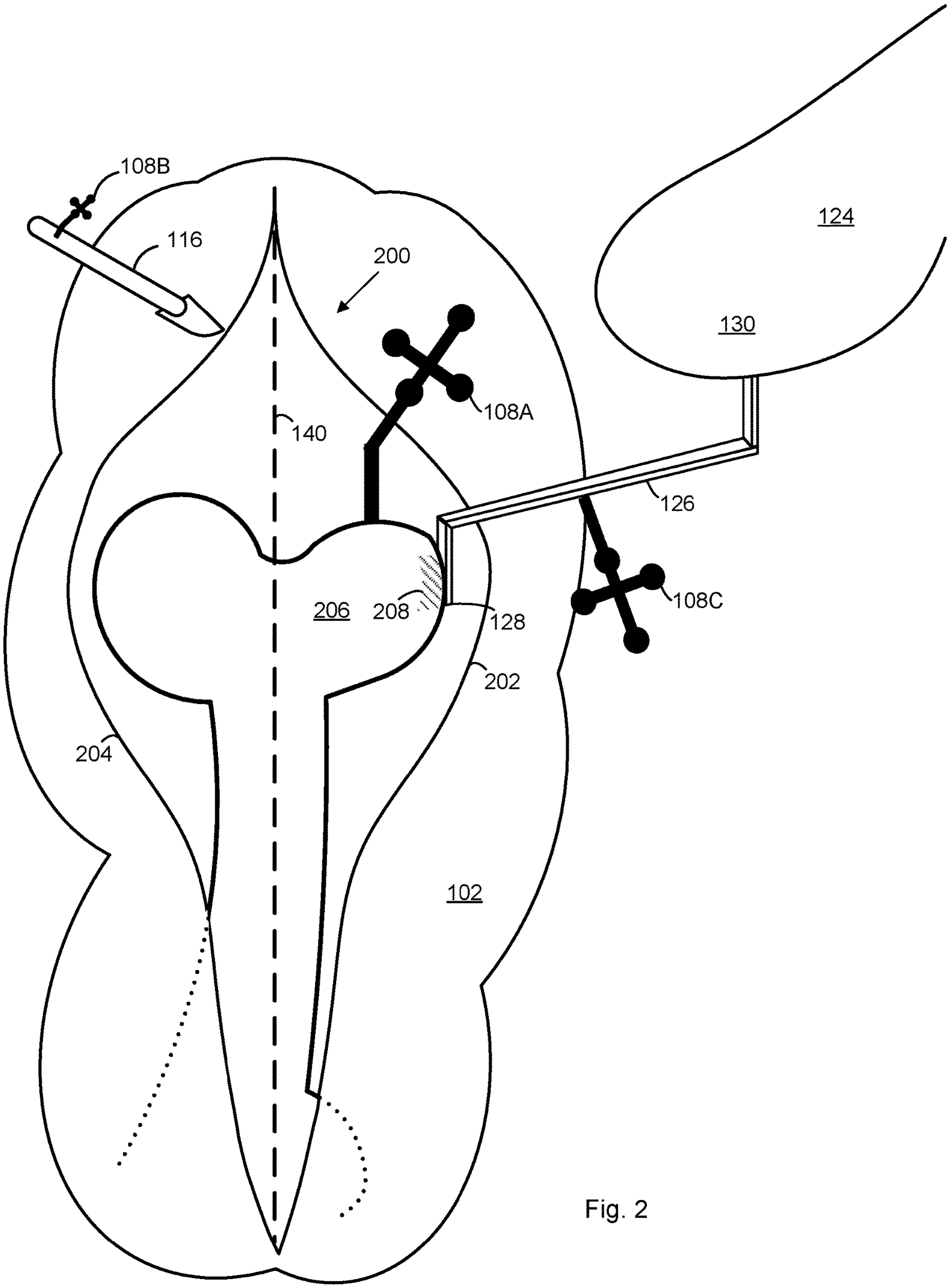
FIG. 2 is an illustration of a portion of a patient including a surgical site showing a robotic retractor engaging with patient anatomy in accordance with an embodiment.

FIG. 2 is an illustration of a portion of patient 102 including a surgical site 200 showing a robotic retractor 126 engaging with the patient 102 in accordance with an embodiment. Incision location 140 shows the initial incision and lines 202 and 204 show the incision as retracted to expose a bone 206, for example, a femur. The portion of the femur in solid lines in the figures denotes an exposed portion and the portion in dotted lines denotes a portion that remains unexposed. Also illustrated in FIG. 2 is a retraction point 208, where a portion of the exposed bone surface is marked with diagonal lines.

In an example, retractor tip 128 engages the patient at a portion of the incision and moves to a second position while remaining engaged. The retractor 126 and its tip 128 are moved by the robot manipulator 120 as commanded. The movement is tracked (e.g. by a localization system including the processing unit 104 and tracking elements (e.g. 108A, 108C). In an example, retractor sensor data is provided to processing unit 104 for processing as further described. Via one or a series of movements between positions, the retractor tip 128 reaches the retraction point 208. In an example, the movements follow a trajectory or path (e.g in one or more segments). Movements may be in up to 6 degrees of freedom. In an example, retractor tip 128 may be positioned at an edge of a bone (e.g. the retraction point 208) and rotated against the bone as a point of leverage to further retract (and maintain retraction) of soft tissue.

FIGS. 3A-3F are illustrations of a portion of a patient 102 showing the surgical site 200 in different stages of a retraction step (which may comprise a series of sub-steps (for example one or more segments of movement) in a surgical procedure in accordance with an embodiment. At FIG. 3A, scalpel 116 with tracking element 108B is tracked to provide an incision location 140. At FIG. 3B the retractor tip 128 is positioned at the incision location 140 (e.g. at a desired portion along the incision location). Double headed arrows show various possible movement directions for the retractor 126 and retractor tip 128 as examples.

Figure 3A:
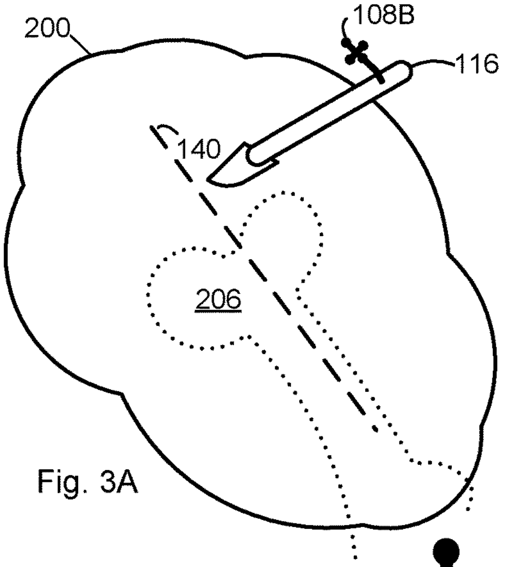
FIGS. 3A, 3B, 3C, 3D, 3E and 3F are illustrations of a portion of a patient showing the surgical site in different stages of a retraction step in a surgical procedure in accordance with an embodiment.
Figure 3B:
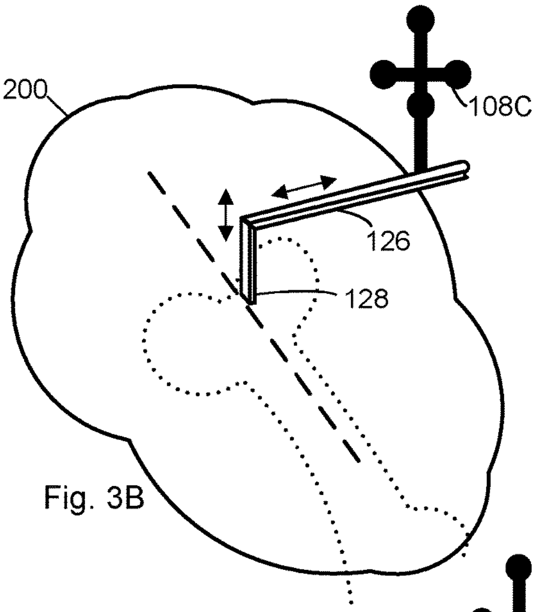
Figure 3C:
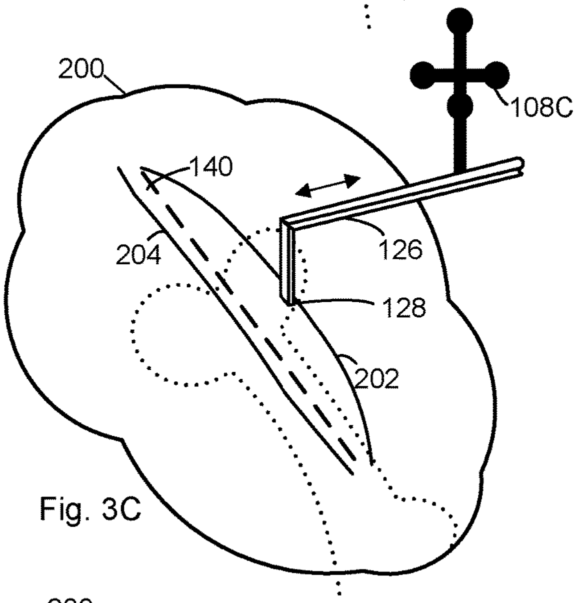

At FIG. 3C the retractor tip 128 is drawn away from the incision location 140 while remaining engaged with the patient (e.g soft tissues), partially opening the surgical site 200. Though not shown, a second or deeper incision may be made at or near incision location 140, typically deeper within soft tissues.

Figure 3D:
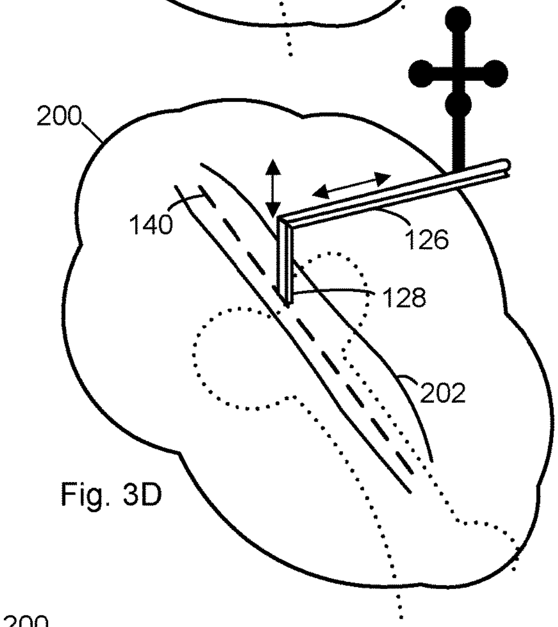
Figure 3E:
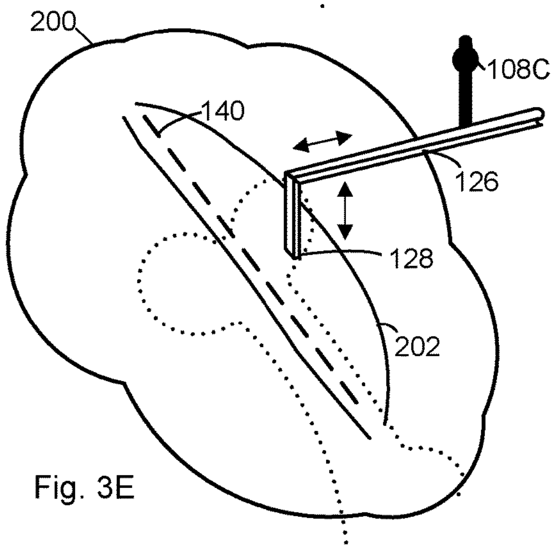

At FIG. 3D, retractor tip 128 is moved back toward the incision location (engagement with the patient may not be maintained throughout due to tissue resilience) and the retractor tip 128 moved deeper into the incision. At FIG. 3E retractor tip 128 is drawn away to further open the site 200. The stages described with reference to FIGS. 3D and 3E can be repeated as needed, to work the retractor tip 128 deeper into the tissue by successive incisions.

Figure 3F:
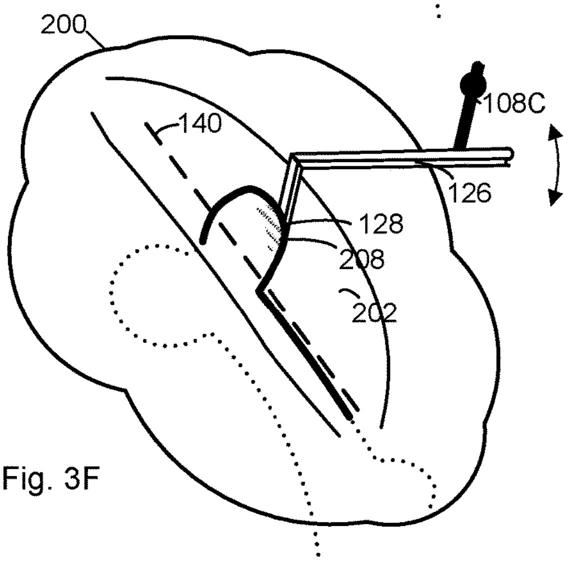

FIG. 3F illustrates the site 200 where at least a portion of the bone 206 is exposed and the retractor tip 128 is engaged at the retraction point 208. Double arrow line shows an example leveraging movement (a rotation) of the retractor 128 and retractor tip 128.

In an example, during the retraction step, processing unit 104 may process tool sensor data received from tool sensor 130. Tool sensor data may provide any of: force, torque and other information regarding the retractor 126 and retractor tip 128. Tool sensor data may be evaluated (processed) to determine a measure of engagement of the retractor 126, particularly retractor tip 128, with patient 102. For example, a sudden drop (a change in value) in the level of engagement may indicate a slippage or other unintended movement of a retracted portion of patient 102 and/or retractor 126. In response, in an embodiment, processing unit 104 is configured to signal a patient engagement message, for example, an error message, in response to the patient engagement measure.

In response, in an embodiment, processing unit 104 is configured to signal or initiate a repositioning sub-step (e.g. via display 111 and or by other output device (speaker, bell, etc.) coupled to the processing unit 104 responsive to a detection of retractor slippage or other unintended movement. A threshold or safety limit to the value of the measure of engagement may be configured for use to compare with the engagement measure. The limit may be configured to vary (e.g. be dynamic) during the retraction step. For example, during a retraction step requiring less force or torque, the threshold or safety limit value may be different from a value for a retraction step requiring greater force or torque. The threshold or safety limit may be a percentage change in value, as an example, indicating a sudden drop of force. In an embodiment, the processing unit is configured to signal any of retractor movement or patient movement responsive to tracking.

Figure 4A:
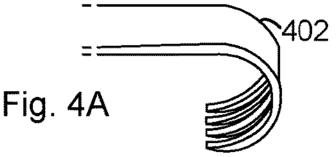
FIGS. 4A and 4B are illustrations that show retractor tips in accordance with respective embodiments.
Figure 4B:
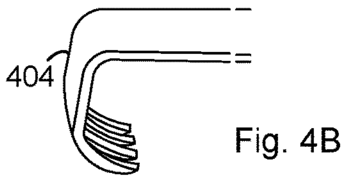

FIGS. 4A and 4B are illustrations that show retractor tips 402, 404 in accordance with respective embodiments. The tips 402, 404 may be shaped to engage with a patient to provide enhanced grip. Thus a retractor 126 may be configured with one of such tips.

Tool sensor data from sensor 130 may be a useful indicator during retractor movement. Retraction sensor data may be a useful indicator when the retractor is not moving but is maintaining a retraction. As noted, retraction point 208 indicates a surface of the bone 206. The retraction point 208 may be used to define a second position where the retractor is directed to move from a first position. In an embodiment, the processing unit may be configured to: i) define a soft tissue retraction parameter relative to the retractor sensor data; and ii) command the robotic manipulator to retract soft tissues at the retraction point in accordance with the soft tissue parameter to maintain the retraction.

In an embodiment, the soft tissue retraction parameter is defined according to more or more of:

- a selection of one of a plurality of default values associated with a patient body type, (e.g. how much soft tissue (e.g. muscle and adipose tissue, etc.) the patient has);
- an initial value provided for user adjustment;
- a value determined during a planning step and received from a planning system (not shown);
- a taring operation wherein realtime retractor sensor data from the retractor sensor is used to define the soft tissue retraction parameter when the retractor tip is completed movement at the second position.

Figure 5A:
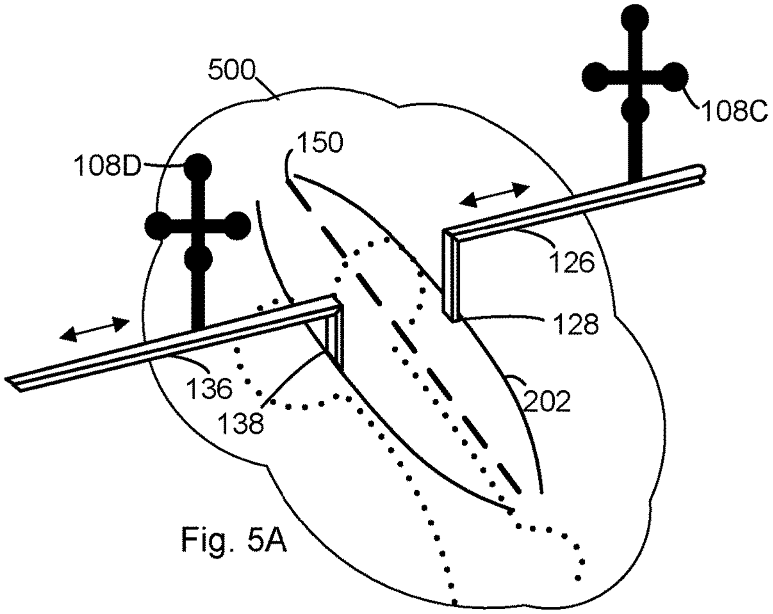
FIGS. 5A and 5B are illustrations of a portion of a patient including a surgical site showing retractors in accordance with respective embodiments.
Figure 5B:
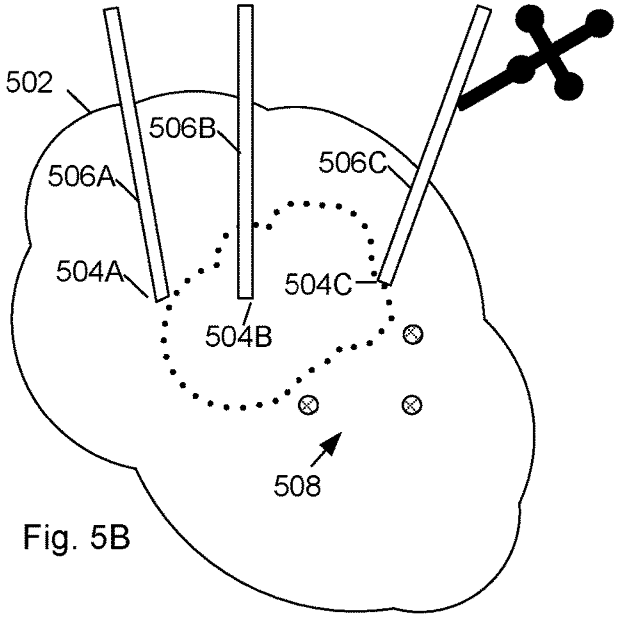

FIGS. 5A and 5B are illustrations of a portion of a patient including a surgical site (500, 502) showing various retractors in accordance with respective embodiments. In FIG. 5A, first and second trackable retractors (126, 136) and respective first and second retractor tips (128, 138) are shown engaging the patient 102 where the second trackable retractor 136 is coupled to tracking element 108D.

In an embodiment, the second trackable retractor 136 is coupled (not shown) for movement by the robotic manipulator 120. In an embodiment, the second trackable retractor 136 is coupled (not shown) for movement by another robotic manipulator (not shown) in communication with processing unit 104. In an embodiment, the processing unit is configured to track each of the trackable retractors and command each of the trackable retractors for movement in engagement with the patient and between respective first and second positions.

In FIG. 5B, in accordance with an embodiment, a surgical procedure is performed in a minimally invasive manner, through various ports 504A, 504B, 504C. The ports 504A, 504B, 504C receive various instruments 506A, 506B, 506C. In an embodiment instrument 506C comprises a trackable retractor coupled to a robotic manipulator (not shown). In an embodiment instrument 506C comprises a trackable distractor coupled to a robotic manipulator (not shown). Patient tracking elements 508 are shown affixed to an external surface of the patient, typically skin. In an embodiment, the processing unit is configured to track the trackable retractor (or distractor as the case may be) and command it for movement in engagement with the patient and between respective first and second positions.

In an embodiment, the retractor (or distractor) may be (initially) positioned in a manual manner through the port 504C.

As noted, processing unit 104, in an embodiment, is configured to i) receive 3D data representing a portion of the patient related to the retraction; and ii) register an association between the 3D data and the patient to determine a position of the retractor relative to the 3D data. The processing unit may be configured to receive second position data representing a location of the second position in the 3D data for the patient. That is the 3D data is associated with position data relative to a 3D position therein (a virtual position). This second position data may be used by the processing unit to command movement of the retractor in the real world 3D space of the operating room, relative to the patient. In an embodiment, the processing unit tracks the position of the retractor relative to the patient to determine an arrival of the retractor tip at the second position.

In an embodiment, the processing unit 104 is configured to display via a display device (e.g. 111) the position of the retractor 126 relative to the 3D data. For example, the position may be displayed as an overlay on 3D data of the patient.

In an embodiment, processing unit 104 is configured to command movement of the trackable retractor to position the retractor tip at the first position in engagement with the patient 102. In an embodiment, the first position is coincident with (at least a portion of) the incision location 140. The processing unit 104 is configured to command the manipulator 120 to move the retractor tip 128 to the first position.

In an embodiment, initially the processing unit 104 does not command movement to the first position. Instead the processing unit 104 commands the robotic manipulator 120 to move to engage with the retractor 126 that is manually pre-positioned with the tip 128 at the first position. The first position may be coincident with (at least a portion of) an incision location 140. Thus, prior to commanding the robotic manipulator 120 to move the retractor tip 128 (e.g. from the first position to the second position), the retractor 128 is not coupled to the manipulator 120. The processing unit 104 is configured to command the manipulator 120 to move to couple with the retractor 128 when the retractor tip 128 is pre-positioned at the first position.

In an embodiment, the processing unit 104 is configured to command movement of the retractor to an insertion depth at the first position.

In an embodiment, insertion depth is determined using tool sensor data for sensor 130 for example. Responsive to the tool sensor data, the retractor tip is positioned within the insertion at the first position until a threshold measure of engagement is achieved. For example, the threshold is responsive to a data value that indicates contact with a bone. In an embodiment, the retractor tip 128 is then moved away (e.g. backed away) from the bone, reducing the insertion depth. Thereafter the processing unit commands movement from the first position to the second position.

In an embodiment, for example as shown in FIG. 3F, it is desired for the retractor tip to contact bone for use as leverage. Thus bone contact and/or bone proximity can be used to guide commands for movement of the trackable tool (e.g retractor 126). Thus, movement to an insertion depth, as an example, may be guided to ensure contact with bone for a retraction step that uses the bone as a fulcrum. Retraction movement may be guided to, avoiding contact with bone/tools, as the case may be.

In an embodiment, insertion depth is determined using 3D data for the patient. In accordance with the registration of the patient and the 3D data and the tracking of the retractor in the patient space, in an example, the relative position of the bone and the retractor tip are determined by the processing unit 104. Movement of the retractor tip to an insertion depth (e.g. which may be a defined distance relative to the bone location, as an example) is commanded. In an embodiment, the movement (and commands therefor) is guided using the relative position.

In an embodiment, the processing unit 104 is configured to monitor sensor data, for example, retractor sensor data, during movement of the retractor. A "spike" in values of the sensor data may indicate contact with a non-soft tissue object such as a bone or a surgical tool (e.g. a femur platform (not shown) of a trackable element (e.g. 108A)). Movement of the retractor may be commanded accordingly (e.g. stop and back away, reposition, etc.).

In an embodiment, retractor sensor data comprises conductive detection or magnetometer data to detect contact or proximity with surgical tools. A responsive signal may be output. Movement of the retractor may be commanded accordingly (e.g. stop and back away, reposition, etc.).

In an embodiment, the processing unit is configured to signal any of retractor movement or patient movement responsive to tracking. For example, during movement, the display screen may change color or output a sound to indicate the retractor is moving. If a patient movement is detected, the display may be updated (e.g. with an informational warning) or a sound may be outputted or both. If the patient movement is material, the processing unit may be configured to stop a procedure step, for example, stopping a movement of the retractor, stopping a workflow, etc.

In an embodiment, the processing unit is configured to command the robot retractor to move the reactor tip along a trajectory or path to the second position.

In respective embodiments, the path is defined according to any one of: i) a path traced by a trackable tool (e.g. a probe) for receiving via the processing unit 104; ii) a path received by the processing unit 104 from a planning system (not shown); iii) one or both of a distance value and direction value relative to the first position e.g. X cm from the first position at an angle or an anatomical direction; iv) one or both of a force and/or torque value and a direction value relative to the first position (e.g. 5 N, etc.); and v) a path defined relative to standard anatomical structures (e.g. muscles) that are expected to be adjacent to the retractor tip 128.

Figure 6C:
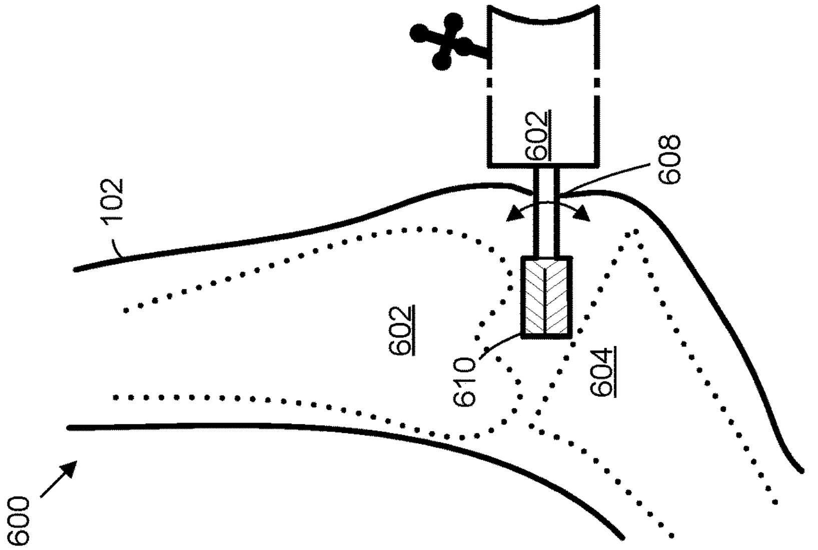
FIGS. 6A, 6B and 6C are illustrations of a portion of a patient including a surgical site showing a robotic distractor engaging with patient anatomy in various stages of a distraction step in accordance with an embodiment.
Figure 6B:
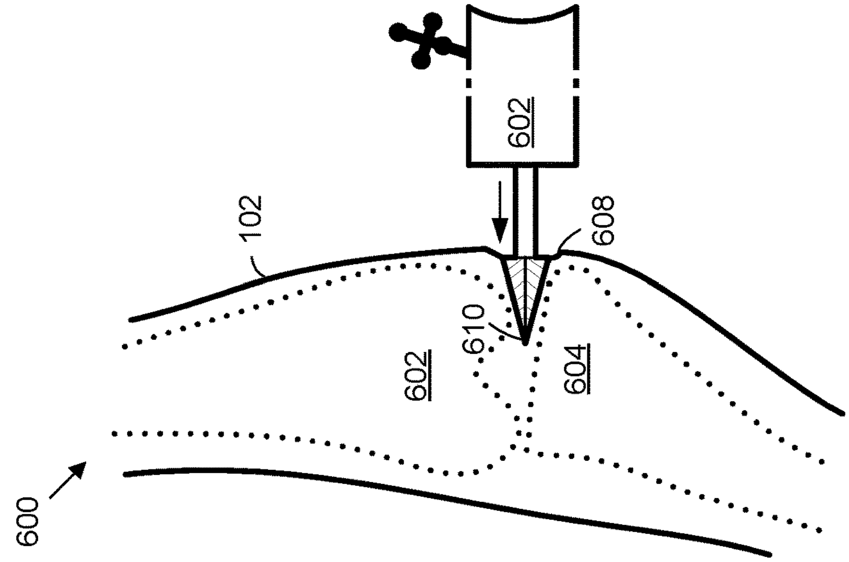
Figure 6A:
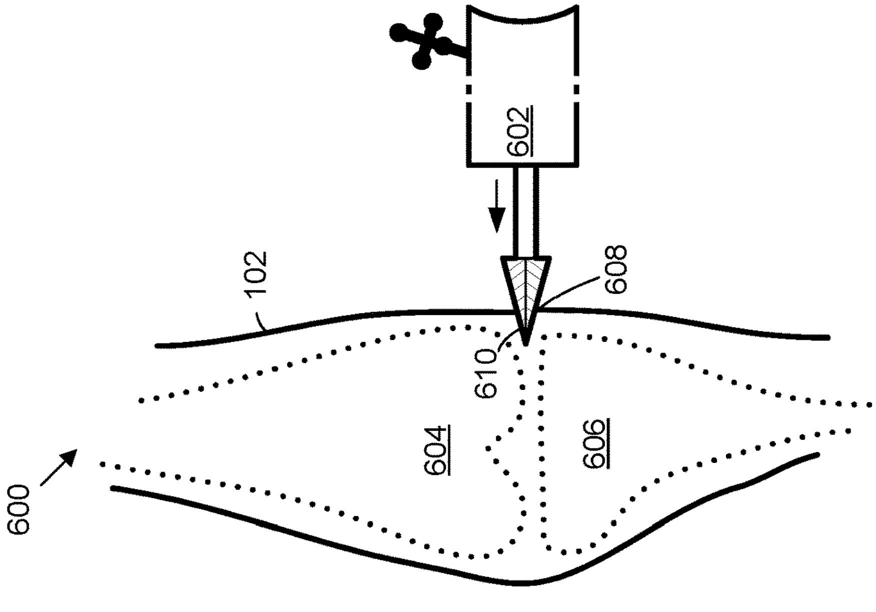

FIGS. 6A, 6B and 6C are illustrations of a portion of a patient 102 including a surgical site 600 showing a trackable distractor 602 coupled to a robotic manipulator (not shown) engaging with patient anatomy in various stages of a distraction step of a surgical procedure in accordance with an embodiment. Surgical site 600 shows a knee joint with a femur 604 and tibia 606. It is desired to distract the bones 604 and 606. A port 608 provides access to the bones for tip 610 of the distractor 602 to be positioned at a desired location between the bones (e.g. a first position).

At FIG. 6B, in an example, the tip 610 is shown at a first position engaging the bones 604, 606. The first position may be determined in the manners as previously described in relation to retraction.

Distractor 602 position (e.g. its tip 610) may be tracked as previously described in relation to retraction and the position (e.g. location or relative position) displayed. The position, for example, may be displayed relative to 3D data of the patient such as via an overlay.

FIG. 6C shows tip 610 at a second position. In the present embodiment, distractor tip 610 comprises a cam or cam like surface where the tip is wider than it is high and is rounded to smoothly engage the bones when rotated through engagement with the patient to push the bones 604, 606 apart.

It will be understood that a series of retraction or distraction sub steps may be performed to complete a retraction or distraction step. The series of sub steps may comprise respective first positions and second positions. The second position of one sub step may serve as the first position of a subsequent sub step. In the distraction example of FIGS. 6A, 6B and 6C, a first position of an initial sub step may be considered to be at engagement with the patient at the port (a point of contact of the tip at the port) and the second position of an initial sub step may be considered to be the position for rotation of the tip where the tip is in a desired location contacting the bones (e.g. at FIG. 6B). Processing unit 104 may command movement accordingly, for example, using sensor data as described for retraction as a measure of engagement, detecting a sufficient engagement with the bones as opposed to only engagement with soft tissues.

In accordance with an embodiment, system 100 (e.g. processing unit) is configurable to present workflow such as via display device 111 and/or other output devices and to receive input via keyboard 112 or other input devices for performing one or more steps of a surgical procedure. The workflow is configured to perform any of:

- prompt and receive registration data to register the patient to the localization system;
- prompt and register an association between the patient and 3D patient image data;
- prompt and receive incision location data with which to determine the first position;
- prompt and receive user input for defining retraction parameters;
- prompt and receive retraction path data via a tracking operation;
- prompt a retraction repositioning procedure following a detection of retraction slippage or unintended movement; and
- prompt and receive user input in relation to further steps of a surgical procedure.

It will be understood that the trackable surgical retractors herein (e.g. 126, 136,) and the trackable surgical distractor (e.g. 506C and 602) are examples of a trackable surgical tool for retraction or distraction as is applicable and such a tool has a tool tip (e.g. 128, 138, 610). It will be understood that a distractor may be associated with a distractor sensor (not shown) like retractor sensor 130 providing distraction data (e.g. force or torque or other data). Such sensors are examples of tool sensors providing tool sensor data.

Figure 7A:
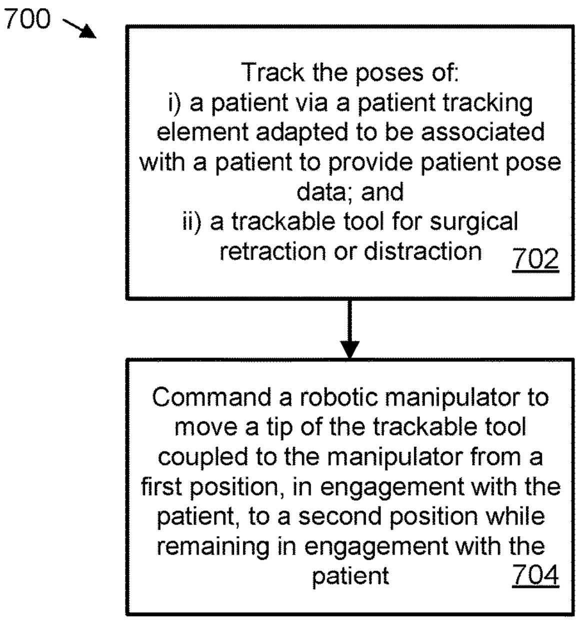
FIGS. 7A, 7B, 7C, 7D, 7E and 7F are flowcharts of respective operations in accordance with respective embodiments.

FIG. 7A is a flowchart of operations 700, in accordance with an embodiment. Operations 700 can be performed by a computing device as described herein. Operations 700 comprise a method, for example, by a processing unit, to automatically perform robotic retraction or distraction with respect to a patient. In the embodiment, at 702, the operations track the poses of: i) a patient via a patient tracking element adapted to be associated with a patient to provide patient pose data; and ii) a trackable tool for surgical retraction or distraction. At 704, operations command a robotic manipulator to move a tip of the trackable tool coupled to the manipulator from a first position, in engagement with the patient, to a second position while remaining in engagement with the patient.

Figure 7B:
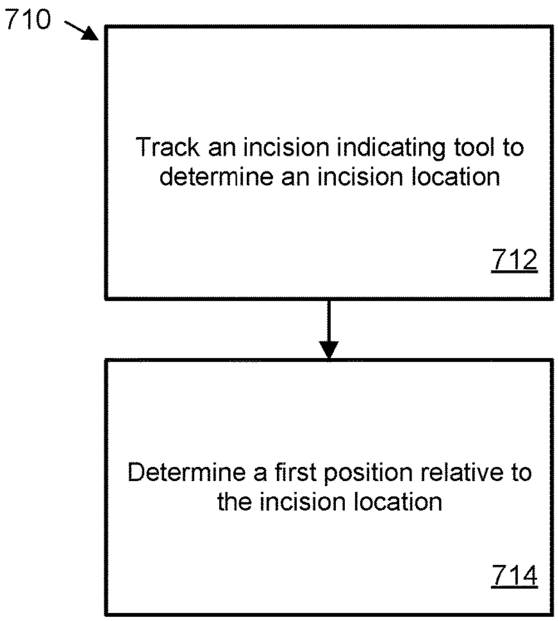

FIG. 7B is a flowchart of operations 710, in accordance with an embodiment. Operations 710 can be performed by a computing device as described herein. Operations 710 (or portions thereof) can be performed in support of (or other association with) operations 700, for example. At 712, operations track an incision indicating tool to determine an incision location. At 714, operations determine a first position relative to the incision location. The first position can be the first position of operations 700, for example.

Figure 7C:
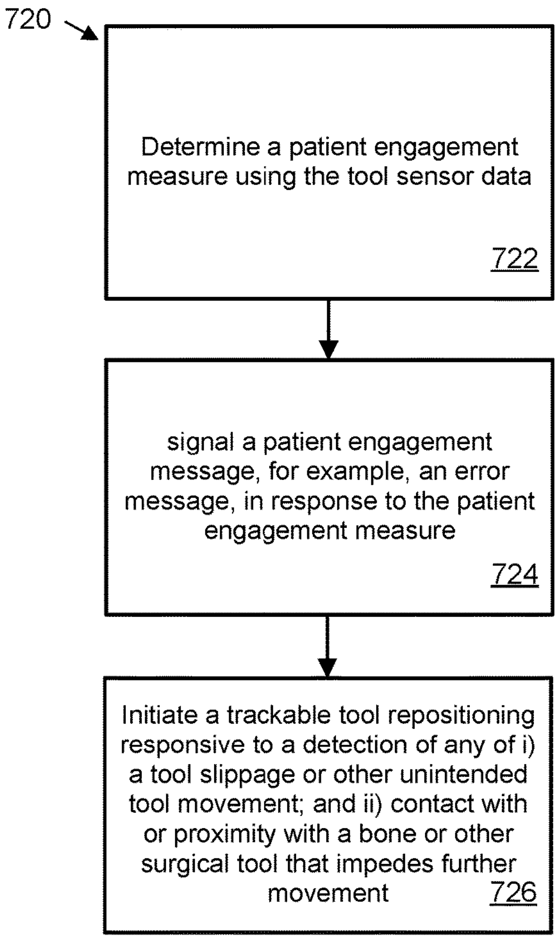

FIG. 7C is a flowchart of operations 720, in accordance with an embodiment. Operations 720 can be performed by a computing device as described herein. Operations 720 (or portions thereof) can be performed in support of (or other association with) operations 700, for example. The trackable tool can be associated with a mechanical tool sensor to provide to the processing unit with tool sensor data associated with the trackable tool. At 722, operations determine a patient engagement measure using the tool sensor data. Optionally, depending on the patient engagement measure/tool sensor data and an evaluation thereof performed by the processing unit, at 724, operations signal a patient engagement message, for example, an error message, in response to the patient engagement measure. The processing unit can perform operations (not shown) to process the tool sensor data to determine and signal any of i) slippage or other unintended tool movement; and ii) contact with or proximity with a bone or other surgical tool that impedes further movement.

In the embodiment, at 726, operations initiate a trackable tool repositioning responsive to a detection of any of i) a tool slippage or other unintended tool movement; and ii) contact with or proximity with a bone or other surgical tool that impedes further movement. Though not shown in the flowcharts, operations of the processing unit, for example, can signal any of trackable tool movement or patient movement responsive to tracking.

Figure 7D:
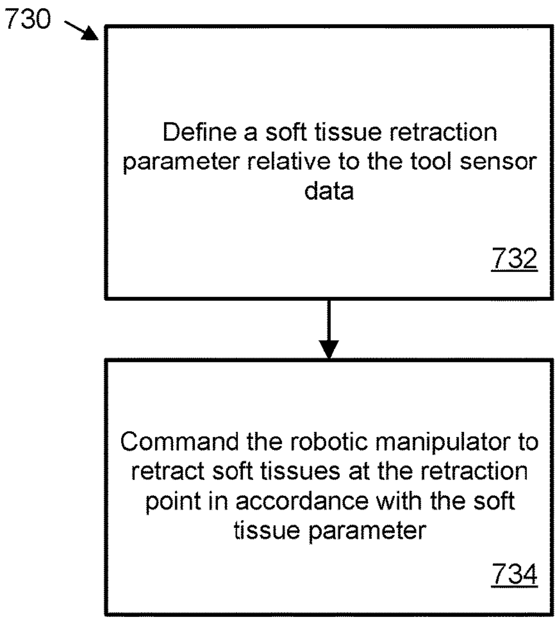

FIG. 7D is a flowchart of operations 730, in accordance with an embodiment. Operations 730 can be performed by a computing device as described herein. Operations 730 (or portions thereof) can be performed in support of (or other association with) operations 700, for example. In the embodiment, the trackable tool is a retraction tool and the second position comprises a retraction point associated with a bone of the patient. At 732, operations define a soft tissue retraction parameter relative to the tool sensor data. At 734 operations command the robotic manipulator to retract soft tissues at the retraction point in accordance with the soft tissue parameter. In embodiments, the soft tissue retraction parameter can be defined according to more or more of: a selection of one of a plurality of default values associated with a patient body type; an initial value provided for user adjustment; a planning value received from a planning system; a taring operation wherein realtime tool sensor data from the tool sensor is used to define the parameter when the tool tip is completed movement at the second position.

Figure 7E:
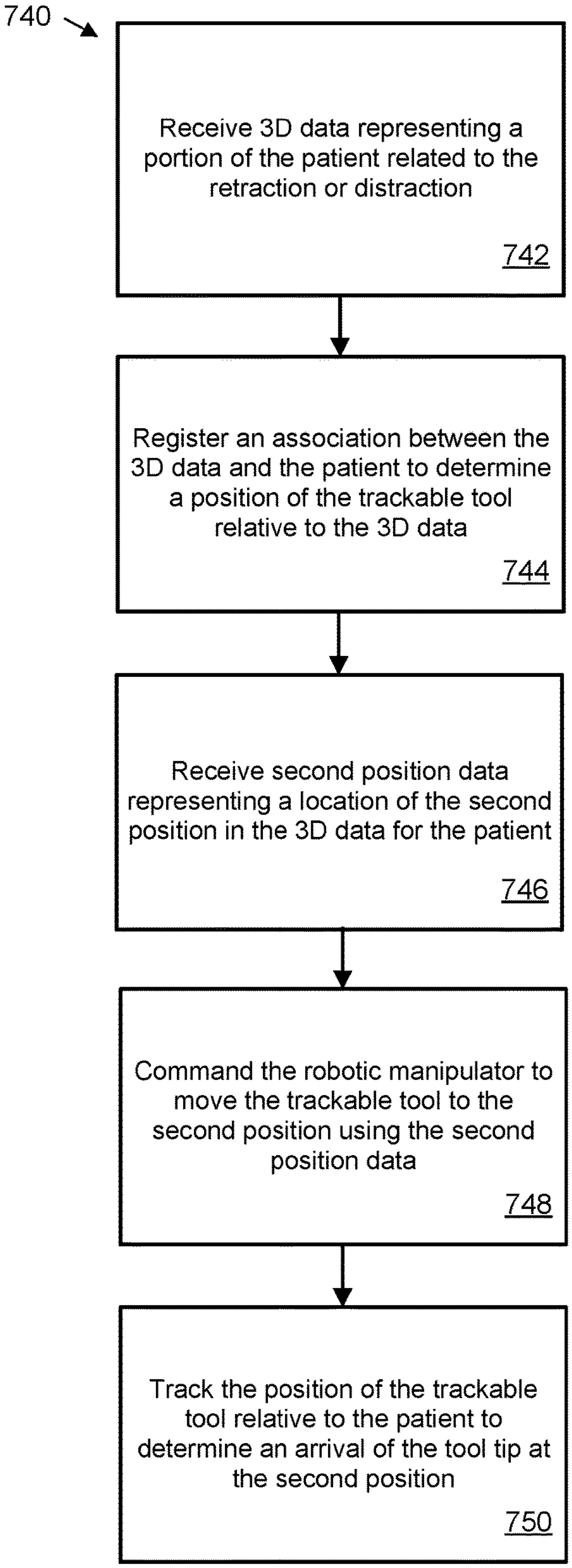

FIG. 7E is a flowchart of operations 740, in accordance with an embodiment. Operations 740 can be performed by a computing device as described herein. Operations 740 (or portions thereof) can be performed in support of (or other association with) operations 700, for example. In the embodiment, at 742, operations receive 3D data representing a portion of the patient related to the retraction or distraction. At 744, operations register an association between the 3D data and the patient to determine a position of the trackable tool relative to the 3D data. At 746, operations receive second position data representing a location of the second position in the 3D data for the patient and at 748, operations command the robotic manipulator to move the trackable tool to the second position using the second position data.

At 750, operations track the position of the trackable tool relative to the patient to determine an arrival of the tool tip at the second position. Though not shown, operations can be configured to display via a display device the position of the trackable tool relative to the 3D data.

In an embodiment, the first position (e.g. in operations 700) can be coincident with at least a portion of an incision location. Though not shown in the flowcharts, operations can command the manipulator to move the tool tip to the first position.

In an embodiment, the first position (e.g. in operations 700) can be coincident with at least a portion of an incision location. Prior to commanding the robotic manipulator to move the tool tip, the trackable tool can be uncoupled to the manipulator. Though not shown in the flowcharts, operations can command the manipulator to move to couple with the trackable tool when the tip is pre-positioned at the first position.

Figure 7F:
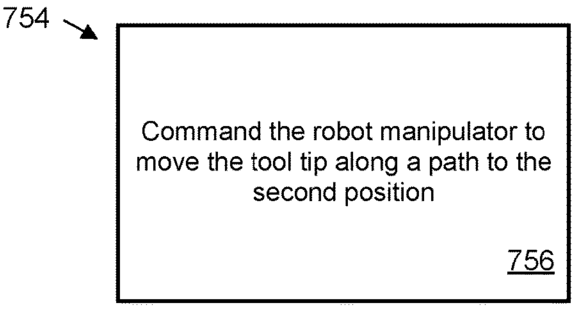

FIG. 7F is a flowchart of operations 754, in accordance with an embodiment. Operations 754 can be performed by a computing device as described herein. Operations 754 (or portions thereof) can be performed in support of (or other association with) operations 700, for example. At 756, operations command the robot manipulator to move the tool tip along a path to the second position. The path can be defined according to any one of: a path traced by another trackable tool for receiving via the processing unit; a path received by the processing unit from a planning system; one or both of a distance value and direction value relative to the first position; one or both of a force and/or torque value and a direction value relative to the first position; and a path defined relative to standard anatomical structures that are expected to be adjacent to the tool tip.

Figure 7G:
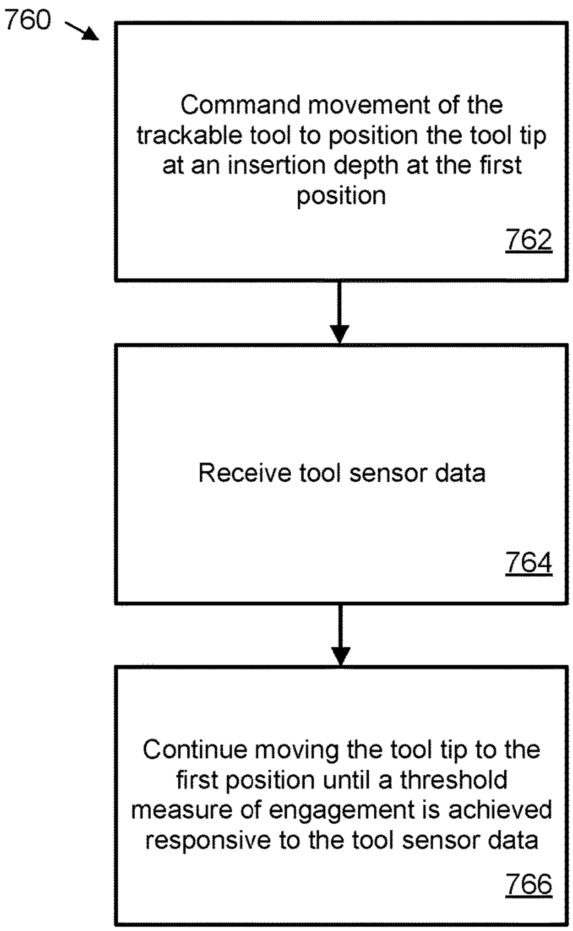

FIG. 7G is a flowchart of operations 760, in accordance with an embodiment. Operations 760 can be performed by a computing device as described herein. Operations 760 (or portions thereof) can be performed in support of (or other association with) operations 700, for example. At 762, operations command movement of the trackable tool to position the tool tip at an insertion depth at the first position. At 764, operations receive tool sensor data at 766, operations cause the tool tip to be positioned at the first position (e.g. continue moving the tool tip) until a threshold measure of engagement is achieved responsive to the tool sensor data.

In an embodiment, though not shown, operations can use bone contact and/or bone proximity as indicated by measured engagement using tool sensor data to guide commands for movement of the trackable tool. In an embodiment, though not shown, operations can determine insertion depth using 3D data for the patient to determine a relative position of a bone and the tool tip and commands movement of the trackable tool using the relative position.

In an embodiment, the trackable tool is a first trackable retractor of a plurality of trackable retractors for movement by the robotic manipulator or another robotic manipulator. Though not shown, operations associated with operations 700 can command each of the trackable retractors for movement in engagement with the patient and between respective first and second positions.

In an embodiment, though not shown, operations associated with operations 700 can present workflow to perform a patient procedure. The workflow can be as previously described herein.

In addition to computing device aspects, a person of ordinary skill will understand that computer program product aspects are disclosed, where instructions are stored in a non-transient storage device (e.g. a memory, CD-ROM, DVD-ROM, disc, etc.) to configure a computing device to perform any of the method aspects stored herein. A processing unit herein can include any form of programmable processor, including a programmable processor. A processing unit can include any one or more of a CPU (central processing unit), GPU (graphics processing unit), microprocessor, FPGA (field programmable gate array), ASIC (application specific integrated circuit) or other processor or unit.

Practical implementation may include any or all of the features described herein. These and other aspects, features and various combinations may be expressed as methods, apparatus, systems, means for performing functions, program products, and in other ways, combining the features described herein. A number of embodiments have been described. Nevertheless, it will be understood that various modifications can be made without departing from the spirit and scope of the processes and techniques described herein. In addition, other steps can be provided, or steps can be eliminated, from the described process, and other components can be added to, or removed from, the described systems. Accordingly, other embodiments are within the scope of the following claims.

Throughout the description and claims of this specification, the word "comprise" and "contain" and variations of them mean "including but not limited to" and they are not intended to (and do not) exclude other components, integers or steps. Throughout this specification, the singular encompasses the plural unless the context requires otherwise. In particular, where the indefinite article is used, the specification is to be understood as contemplating plurality as well as singularity, unless the context requires otherwise.

Features, integers characteristics, compounds, chemical moieties or groups described in conjunction with a particular aspect, embodiment or example of the invention are to be understood to be applicable to any other aspect, embodiment or example unless incompatible therewith. All of the features disclosed herein (including any accompanying claims, abstract and drawings), and/or all of the steps of any method or process so disclosed, may be combined in any combination, except combinations where at least some of such features and/or steps are mutually exclusive. The invention is not restricted to the details of any foregoing examples or embodiments. The invention extends to any novel one, or any novel combination, of the features disclosed in this specification (including any accompanying claims, abstract and drawings) or to any novel one, or any novel combination, of the steps of any method or process disclosed.

What is claimed is:

1. A robotic surgery system to automatically perform robotic retraction with respect to a patient comprising:
- a patient tracking element adapted to be associated with a patient to provide patient pose data;
- a trackable tool comprising a retractor having a retractor tool tip for surgical retraction;
- a robotic manipulator configured to couple to the trackable tool and move the trackable tool under command; and
- a processing unit configured to:
  - track the poses of:
    - the patient via the patient tracking element; and
    - the trackable tool including the retractor tool tip; and
  - define a retraction point associated with a bone of the patient, the retraction point defining a point of leverage against the bone for the trackable tool;
  - command the robotic manipulator to move the trackable tool coupled to the manipulator from a first position with retractor tool tip in engagement with the bone of the patient at the retraction point, to a second position with retractor tool tip remaining in engagement with the patient at the retraction point to retract a soft tissue for bone exposure.

2. The system of claim 1 comprising an incision indicating tool trackable by the processing unit and wherein the processing unit is configured to:

further track the incision indicating tool to determine an incision location; and determine the first position relative to the incision location.

3. The system of claim 2, wherein the incision indicating tool is one of:

a soft tissue cutting tool and the incision location is determined in response to the soft tissue cutting tool making an incision or tracing an incision; or a probe and the incision location is determined in response to the probe indicating the incision location.

4. The system of claim 1 comprising:

a mechanical tool sensor to provide the processing unit with tool sensor data associated with the trackable tool, the tool sensor data comprising one or more of:

force information for a force applied to the trackable tool;

torque information for a torque applied to the trackable tool; or state information for a state of the trackable tool; and wherein the processing unit is configured to:

receive and process the tool sensor data to determine a patient engagement measure indicating the engagement of the retractor tip with the soft tissue at the retraction point; and, determine and signal a slippage of the trackable tool at the retraction point a sudden change in engagement as represented by the patient engagement measure.

5. The system of claim 4, wherein the processing unit is configured to signal a patient engagement message in response to the patient engagement measure.

6. The system of claim 4, wherein the processing unit is configured to process the tool sensor data to determine and signal any of i) unintended tool movement; or ii) contact with or proximity to another bone or other surgical tool that impedes further movement.

7. The system of claim 4, wherein the processing unit is configured to initiate a trackable tool repositioning responsive to the detection of tool slippage.

8. The system of claim 1, wherein the processing unit is configured to signal any of trackable tool movement or patient movement responsive to tracking.

9. The system of claim 1, wherein the processing unit is configured to:

command the robotic manipulator to retract soft tissues by rotating the trackable tool with the tip against the bone at the retraction point providing the point of leverage.

10. The system of claim 9, wherein:

the processing unit is configured to:

define a soft tissue retraction parameter relative to the tool sensor data and control the retracting and maintaining of the soft tissue retraction at the retraction point using the soft tissue retraction parameter; and the soft tissue retraction parameter is defined according to one or more of:

a selection of one of a plurality of default values associated with a patient body type;

an initial value provided for user adjustment;

a planning value received from a planning system; or a taring operation wherein real time tool sensor data from the tool sensor is used to define the parameter responsive to a completion of movement by the retractor tool tip at the second position.

11. The system of claim 1, wherein the processing unit is configured to:

receive 3D data representing a portion of the patient related to the retraction; and register an association between the 3D data and the patient to determine a position of the trackable tool relative to the 3D data.

12. The system of claim 11, wherein the processing unit is configured to receive second position data representing a location of the second position in the 3D data for the patient.

13. The system of claim 12, wherein the processing unit is configured to command the robotic manipulator to move the trackable tool to the second position using the second position data.

14. The system of claim 13, wherein the processing unit tracks the position of the trackable tool relative to the patient to determine an arrival of the retractor tool tip at the second position.

15. The system of claim 11, wherein the processing unit is configured to display via a display device the position of the trackable tool relative to the 3D data.

16. The system of claim 1, wherein the processing unit is configured to command the robot manipulator to move the retractor along a path to the second position, the path comprising one or more path segments to position the retractor at the first position with the retractor tool tip at the retraction point and move the retractor to the second position with the retractor tool tip remaining at the retraction point.

17. The system of claim 16, wherein the path is defined according to one of:

a path received by the processing unit from a planning system.

18. The system of claim 1, wherein, the processing unit is configured to command movement of the trackable tool to position the retractor tool tip at an insertion depth at the first position.

19. The system of claim 18, wherein the insertion depth is determined using tool sensor data and the retractor tool tip is positioned at the first position until a threshold measure of engagement is achieved responsive to the tool sensor data.

20. The system of claim 19, wherein the processing unit is configured to use bone contact and/or bone proximity as indicated by measured engagement using tool sensor data to guide commands for movement of the trackable tool.

21. The system of claim 18, wherein the processing unit determines insertion depth using 3D data for the patient to determine a relative position of a bone and the retractor tool tip and commands movement of the trackable tool using the relative position.

22. The system of claim 1, wherein the trackable tool is a first trackable retractor of a plurality of trackable retractors for movement by the robotic manipulator or another robotic manipulator and wherein the processing unit is configured to track each of the trackable retractors and command each of the trackable retractors for movement in engagement with the patient and between respective first and second positions.

23. The system of claim 1, wherein the system defines a localization system.

* * * * *